(12) United States Patent
Syson et al.

(10) Patent No.: US 10,556,247 B2
(45) Date of Patent: *Feb. 11, 2020

(54) DISPENSER

(71) Applicant: Ecolab USA Inc., St. Paul, MN (US)

(72) Inventors: Paul Syson, Derbyshire (GB); Neil Simpson, Tonypandy (GB); James Tucker, Camberley (GB); Karen Rossington, Thame (GB)

(73) Assignee: Ecolab USA Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/477,875

(22) Filed: Apr. 3, 2017

(65) Prior Publication Data

US 2017/0304855 A1 Oct. 26, 2017

Related U.S. Application Data

(63) Continuation of application No. 14/939,810, filed on Nov. 12, 2015, now Pat. No. 9,649,648, which is a
(Continued)

(51) Int. Cl.
*B05B 11/00* (2006.01)
*A61L 2/08* (2006.01)

(52) U.S. Cl.
CPC ...... *B05B 11/0044* (2018.08); *B05B 11/0037* (2013.01); *B05B 11/0039* (2018.08);
(Continued)

(58) Field of Classification Search
CPC ............. B05B 11/0016; B05B 11/0018; B05B 11/0037; B05B 11/0043; B05B 11/3042;
(Continued)

(56) References Cited

U.S. PATENT DOCUMENTS

| 4,930,667 A * | 6/1990 | Holzner, Sr. ......... A47K 5/1209 222/189.09 |
| 5,074,440 A | 12/1991 | Clements et al. |

(Continued)

FOREIGN PATENT DOCUMENTS

| DE | 10 2004 050 679 | 4/2006 |
| DE | 10 2008 034 244 | 3/2010 |

(Continued)

OTHER PUBLICATIONS

Extended European Search Report for EP 17205262.3, dated Mar. 15, 2018.
(Continued)

*Primary Examiner* — Jeremy Carroll
(74) *Attorney, Agent, or Firm* — Merchant & Gould P.C.

(57) ABSTRACT

A spray dispenser is provided, the spray dispenser comprising a container for holding a liquid to be dispensed and a dispensing assembly for extracting liquid from said container, the dispensing assembly comprising a pressure-relief valve for release of excessive pressure in the container and a filter arranged to permit egress of gas through the filter, inhibit egress of liquid from the container and to inhibit ingress of contaminants into the container through the pressure relief valve. A dispensing assembly for use is a spray dispenser is also provided.

38 Claims, 7 Drawing Sheets

Related U.S. Application Data continuation of application No. 13/502,954, filed as application No. PCT/GB2010/051761 on Oct. 19, 2010, now Pat. No. 9,211,557.

(52) U.S. Cl.
CPC .. B05B 11/00412 (2018.08); B05B 11/00442 (2018.08); B05B 11/3042 (2013.01); B05B 11/3052 (2013.01); *A61L 2/081* (2013.01); *A61L 2202/23* (2013.01); *B05B 11/3011* (2013.01)

(58) Field of Classification Search
CPC ............. B05B 11/3052; B05B 11/3011; B05B 11/0021; A61L 2/081; A61L 2202/23
USPC ...................................... 222/189, 382, 382.1
See application file for complete search history.

(56) References Cited

U.S. PATENT DOCUMENTS

| | | | |
|---|---|---|---|
| 5,183,184 A | 2/1993 | Rannalletta et al. | |
| 5,398,846 A * | 3/1995 | Corba | B05B 11/0016 222/1 |
| 5,752,629 A | 5/1998 | Hardy | |
| 5,927,559 A | 7/1999 | Bommer et al. | |
| 6,073,812 A | 6/2000 | Wade et al. | |
| 9,211,557 B2 | 12/2015 | Syson | |
| 2002/0064477 A1 | 5/2002 | Vellutato | |
| 2004/0261868 A1 | 12/2004 | Secondo | |
| 2005/0127107 A1* | 6/2005 | Mbonyumuhire | B05B 11/0016 222/383.1 |
| 2005/0258272 A1 | 11/2005 | Salvage | |
| 2006/0065677 A1 | 3/2006 | Py et al. | |
| 2007/0102455 A1 | 5/2007 | Stark et al. | |
| 2007/0262090 A1 | 11/2007 | Ritsche | |
| 2007/0284393 A1* | 12/2007 | Ritsche | B05B 11/0016 222/189.09 |
| 2009/0101680 A1 | 4/2009 | Laws et al. | |
| 2010/0116852 A1 | 5/2010 | Painchaud et al. | |
| 2010/0147899 A1 | 6/2010 | Nardi | |
| 2011/0155770 A1 | 6/2011 | Painchaud et al. | |
| 2012/0067926 A1 | 3/2012 | Ishikawa et al. | |
| 2012/0223106 A1 | 9/2012 | Painchaud et al. | |
| 2012/0305599 A1 | 12/2012 | Painchaud et al. | |

FOREIGN PATENT DOCUMENTS

| | | |
|---|---|---|
| EP | 0 379 047 | 7/1990 |
| EP | 1 454 839 | 9/2004 |
| GB | 1 563 749 | 3/1980 |
| GB | 2 106 877 | 4/1983 |
| GB | 2 333 129 | 7/1999 |
| GB | 2 391 862 | 2/2004 |
| GB | 2 391 862 A | 2/2004 |
| JP | H 0 634 759 U | 5/1994 |
| JP | H 08 252 509 A | 10/1996 |
| JP | H 0 851 0395 A | 11/1996 |
| JP | 2 000 507 532 A | 6/2000 |
| JP | 2 003 266 073 A | 9/2003 |
| WO | WO 93/10015 | 5/1993 |
| WO | 2008/072041 A1 | 6/2008 |

OTHER PUBLICATIONS

International Search Report and Written Opinion from International Application No. PCT/GB2010/051761 dated Mar. 29, 2011.
Search Report from United Kingdom Application No. GB0918296.5.
Liesl K. Massey, The Effects of Sterilization Methods on Plastics and Elastomers: the Definitive User's Guide and Databook, second edition, "Introduction to Sterilization Methods"; "Acetal (Polyoxymethylene)"; pp. 1-18, 2005.
Extended European Search Report for Application No. 18213218.3 dated Apr. 29, 2019.

* cited by examiner

DISPENSER

Cross Reference to Related Applications

This application is a continuation of U.S. application Ser. No. 14/939,810, filed 12 Nov. 2015, issued as U.S. Pat. No. 9,649,648, which is a continuation of U.S. application Ser. No. 13/502,954, filed 26 Sep. 2012, issued as U.S. Pat. No. 9,211,557, which is a National Stage Application of PCT/GB2010/051761, filed 19 Oct. 2010, which claims benefit of Ser. No. 0918286.5, filed 19 Oct. 2009 in the United Kingdom and which applications are incorporated herein by reference. To the extent appropriate, a claim of priority is made to each of the above disclosed applications.

FIELD

The present invention relates to a spray dispenser, particularly (but not exclusively) for use in dispensing sterile fluids.

BACKGROUND

GB2391862 discloses a dispenser which is effective for dispensing sterile liquids. The dispenser comprises a collapsible inner vessel from which liquid is dispensed using a trigger-actuated pumping arrangement and a dip tube which extends to the bottom of the inner vessel, the inner vessel being located in a rigid outer bottle. As liquid is dispensed from the collapsible vessel, the vessel collapses because no ingress of air is permitted into the vessel through the dispensing arrangement. Air is permitted to enter the space between the inner vessel and outer bottle. Such dispensers may be sterilised by filling the dispenser with fluid, sealing the dispenser in an air-tight bag (and optionally sealing this air-tight bag within a second and optionally a third air tight bag) and then irradiating the dispenser to sterilise the dispenser and its contents. In certain circumstances, irradiation may cause unwanted side effects. For example, irradiation causes unwanted generation of gas in the container. Such generation of gas may cause unwanted bulging of the container due to a pressure build-up in the container and the container being made of sub-standard materials. For example, the bottom of the outer container may bulge outwards, producing a bottle with a rounded bottom which cannot stand. Alternatively, leakage may be observed from one of several potentially weak points; unwanted leakage may be observed through the dispensing valve.

The present invention seeks to mitigate one or more of the problems mentioned above and/or to provide an improved spray dispenser.

SUMMARY

In accordance with a first aspect of the present invention, there is provided a spray dispenser comprising a container for holding a liquid to be dispensed and a dispensing assembly for extracting liquid from said container, the dispensing assembly comprising a pressure-relief valve for release of excessive pressure in the container and a filter arranged to permit egress of gas from the container through the filter and through the pressure-relief valve, the filter inhibiting egress of liquid from the container through the filter.

The spray dispenser of the present invention provides a dispenser particularly suitable for the dispensing of sterile liquids because it permits release of excessive pressure (such as may occur when the liquid contained in the container is irradiated to sterilise the container and its contents), the valve closing when said pressure has been relieved, thus inhibiting ingress of contaminants into the container. Furthermore, the filter inhibits egress of liquid from the container, therefore decreasing the likelihood of any spillage in the event that an overpressure occurs in the container. It is preferred that the pressure-relief valve is closed in the absence of excessive pressure to inhibit ingress of air and contaminants into the container. This is of particular benefit if it is undesirable to allow air into the container, for example, if the container comprises a collapsible liquid-containing portion.

Filters which are typically used in the spray dispenser of the present invention also typically inhibit ingress of contaminants into the container through the pressure relief valve.

For the avoidance of confusion, it is hereby stated that the pressure-relief valve is not a dispensing valve (i.e. a valve through which liquid is, in use, dispensed). The spray dispenser of the present invention will typically be provided with a dispensing valve in addition to the pressure-relief valve.

The filter typically prevents passage therethrough of liquid at the pressures which typically build-up within a container. These pressures are discussed below.

The filter may be permeable to gas and impermeable to liquids.

Those skilled in the art will realise that the filter will be impermeable to the liquid held within a container at the pressures generated when such filled containers are subjected to sterilising irradiation. Typical pressures are those generated when 1 litre of isopropyl alcohol contained within a container designed to contain 1 litre of liquid is subjected to 25 kGy of gamma radiation emitted by a cobalt source. The headspace above 1 litre of liquid is estimated to be approximately 20-30 ml.

Those skilled in the art will readily be able to determine whether a filter is impermeable to liquid by observing whether liquid permeates through a filter.

Those skilled in the art will realise that the liquid is not an essential (but rather an optional) part of the spray dispenser of the present invention.

It is preferred that the filter is in a gas flow path between the interior of the container and the pressure-relief valve. Alternatively, the pressure-relief valve may be in a gas flow path between the interior of the container and the filter.

The filter preferably inhibits ingress of particulate into the container. The filter may comprise pores which permit passage therethrough of vapour, but inhibit passage therethrough of particulate. It is preferred that the filter inhibits passage therethrough of particles having a mean dimension of greater than 50 microns, more preferably greater than 5 microns and further more preferably 0.5 microns. The pores may have a mean greatest dimension of less than 10 microns, preferably less than 5 microns, more preferably less than 1 micron and further more preferably less than 0.3 microns. Alternatively, the filter may be substantially free of pores.

The filter may comprise a membrane. The membrane may be hydrophobic, and may comprise a hydrophobic material such as polytetrafluoroethylene. Alternatively, the membrane may be oleophobic.

The filter may be located within a filter housing.

The container may comprise a fluid containment portion which may be collapsible (for example, the container may comprise a collapsible bag, typically made from plastics material). The container may comprise a container seal-forming surface. The spray dispenser may comprise a sealing member for forming a seal against the container seal-forming surface to inhibit ingress of air into the container. The sealing member may be provided as part of the dispensing assembly.

The container may be sufficiently rigid that it does not collapse when liquid is extracted therefrom.

The sealing member may be annular.

The container seal-forming surface may be provided by a collar. If the container comprises a collapsible fluid containment portion, it is preferred that the collar is more rigid than the fluid containment portion.

The pressure-relief valve may comprise any suitable one-way valve. The pressure-relief valve may comprise a spring valve, a diaphragm valve, a butterfly valve, a swing valve, a ball check valve or a duckbill valve. The duckbill valve is preferred because it may show good performance. The operation of the pressure-relief valve should preferably not be adversely affected by gamma radiation, such as is typically used to sterilise the contents of a container. The characteristics of the pressure-relief valve may be selected so that, after releasing excess pressure within the container, the valve closes appropriately to inhibit ingress of air into the container. This is particularly preferred, for example, if the container is collapsible.

As mentioned above, a container is typically subjected to a 25 kGy sterilising dose. For example, if the pressure-relief valve comprises a duckbill valve, the duckbill valve should be made from a material whose performance is not affected by the sterilisation process to the extent that the duckbill valve does not function appropriately. For example, duckbill valves may be made from elastomers whose properties are not significantly affected by irradiation. Details of such elastomers will be readily apparent to those skilled in the art. For example, details of such elastomers may be found in "The effects of sterilization methods on plastics and elastomers: the definitive user's guide and databook", edited by L. K. Massey, published by William Andrew, 2004.

The spray dispenser may be provided with a closure means, such as a cap, for inhibiting access to the container. One or both of the pressure-relief valve and filter may be associated with the closure means. The dispensing assembly may comprise the closure means. For example, the closure means may be provided with both the pressure-relief valve and the filter.

The spray dispenser preferably comprises a housing for enclosing the container. The housing may support the container; this is particularly preferred if the container comprises a collapsible fluid containing portion. The closure means, if present, may be removably attachable to the housing. This is particularly preferable if the closure means is provided as part of the dispensing assembly. For example, the closure means may be provided with a configuration which interacts with a corresponding configuration provided on the housing so as to permit attachment of the closure means to the housing.

The dispensing assembly may comprise a pressure means for creating a differential pressure to dispense fluid from the container. The dispensing assembly may comprise an actuator, such as a trigger pumping arrangement.

The dispensing assembly may comprise a dispensing line, such as an elongate tube.

The dispensing line, if present, may be in a gas-tight sealing engagement with a dispensing line sealing means. The dispensing line sealing means inhibits ingress of air into the container. The dispensing line sealing means may be provided by the above-mentioned sealing member. The dispensing line sealing means may be provided as part of the dispensing assembly.

Alternatively, the dispensing line sealing means may be provided by a separate component. For example, the dispensing line sealing means may be in the form of an apertured plate, the plate being provided with an aperture which receives the dispensing line in sealing engagement. The apertured plate may be associated with (and may be adjacent or proximate to) the closure means (if present).

The dispensing assembly may comprise one or both of a dispensing line and a pressure means for creating differential pressure to dispense fluid.

The dispensing assembly may be mountable onto, and optionally dismountable from, the container.

In accordance with a second aspect of the present invention, there is provided a dispensing assembly for use in the spray dispenser assembly of the first aspect of the invention. The dispensing assembly of the second aspect of the present invention may comprise those features mentioned above in relation to the spray dispenser of the first aspect of the present invention.

In accordance with a third aspect of the present invention, there is provided a dispensing assembly for use in a spray dispenser to dispense liquid from a container, the dispensing assembly comprising a pressure-relief valve for release of excessive pressure in a container to which the dispensing assembly is fitted and a filter arranged to permit egress of gas from the container through the filter and through the pressure-relief valve, the filter inhibiting egress through the filter of liquid from a container to which the dispensing assembly is fitted.

For the avoidance of confusion, it is hereby stated that the pressure-relief valve is not a dispensing valve (i.e. a valve through which liquid is, in use, dispensed). The dispensing assembly of the present invention will typically be provided with a dispensing valve in addition to the pressure-relief valve.

The filter typically used in the dispensing assembly is capable of inhibiting ingress of contaminants into a container to which the dispensing assembly is fitted.

The dispensing assembly of the third aspect of the present invention may comprise those features described above in relation to the spray dispenser of the first aspect of present invention. Furthermore, the dispensing assembly of the third aspect of the present invention may be suitable for use in the spray dispenser of the first aspect of the present invention.

For example, the dispensing assembly of the third aspect of the present invention may comprise a closure means for inhibiting access to a container. The dispensing assembly may comprise a dispensing aperture. The dispensing assembly may comprise a dispensing line in fluid communication with the dispensing aperture. The dispensing assembly may comprise a pressure means for creating differential pressure to dispense liquid.

BRIEF DESCRIPTION OF THE DRAWINGS

The present invention will be described by way of example only with reference to the following figures of which.

DETAILED DESCRIPTION

Figure 1:
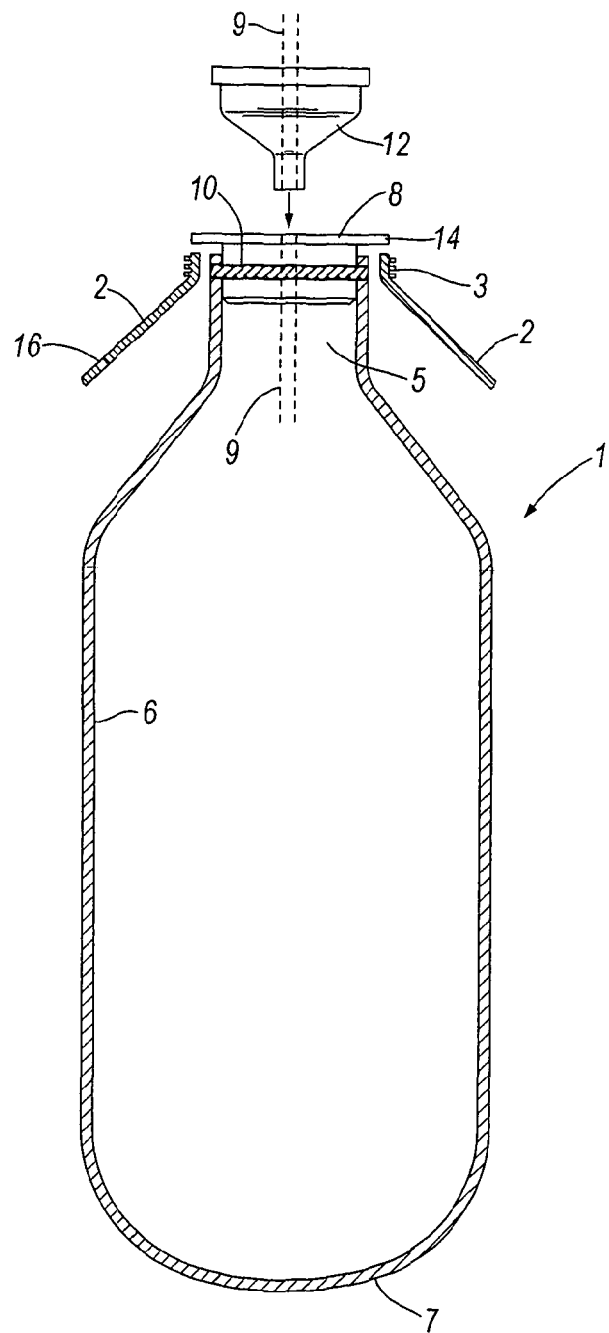
FIG. 1 is an exploded view of part of a known dispenser.
Figure 2:
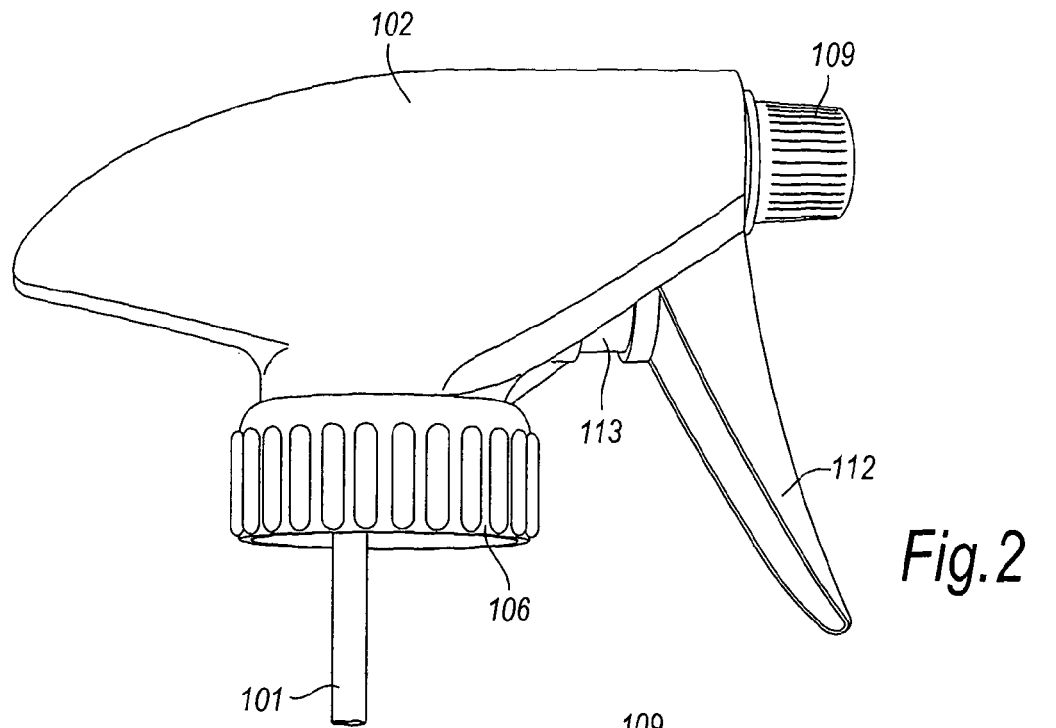
FIG. 2 is a side-on view of part of an example of a dispenser in accordance with the present invention.
Figure 3:
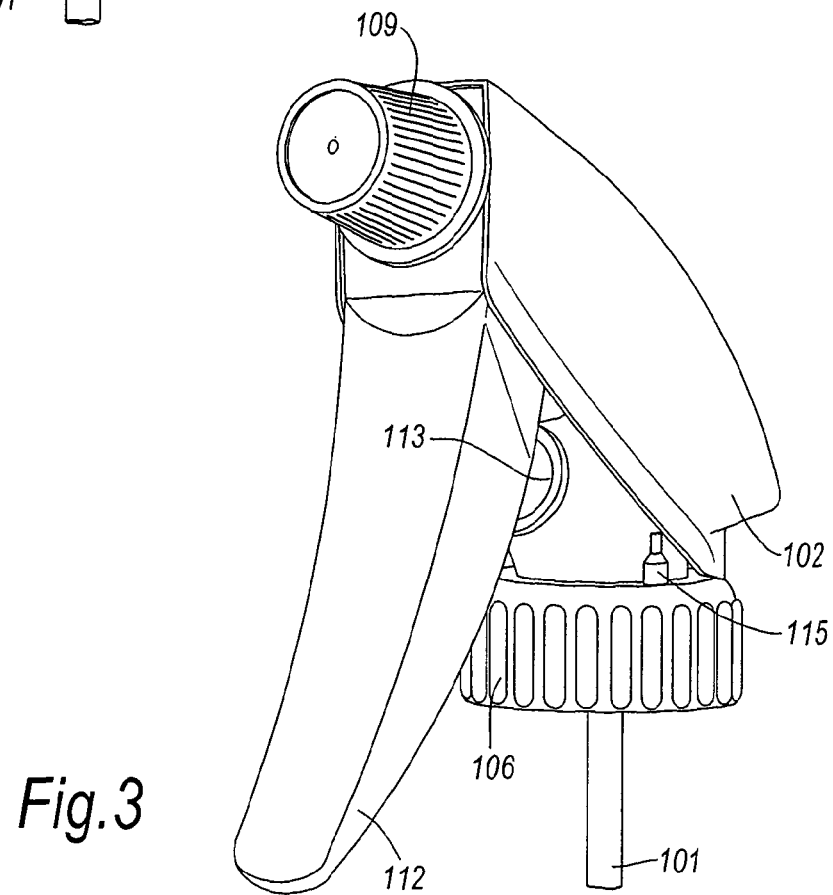
FIG. 3 is a perspective view of the part of the dispenser shown in FIG. 2.
Figure 4:
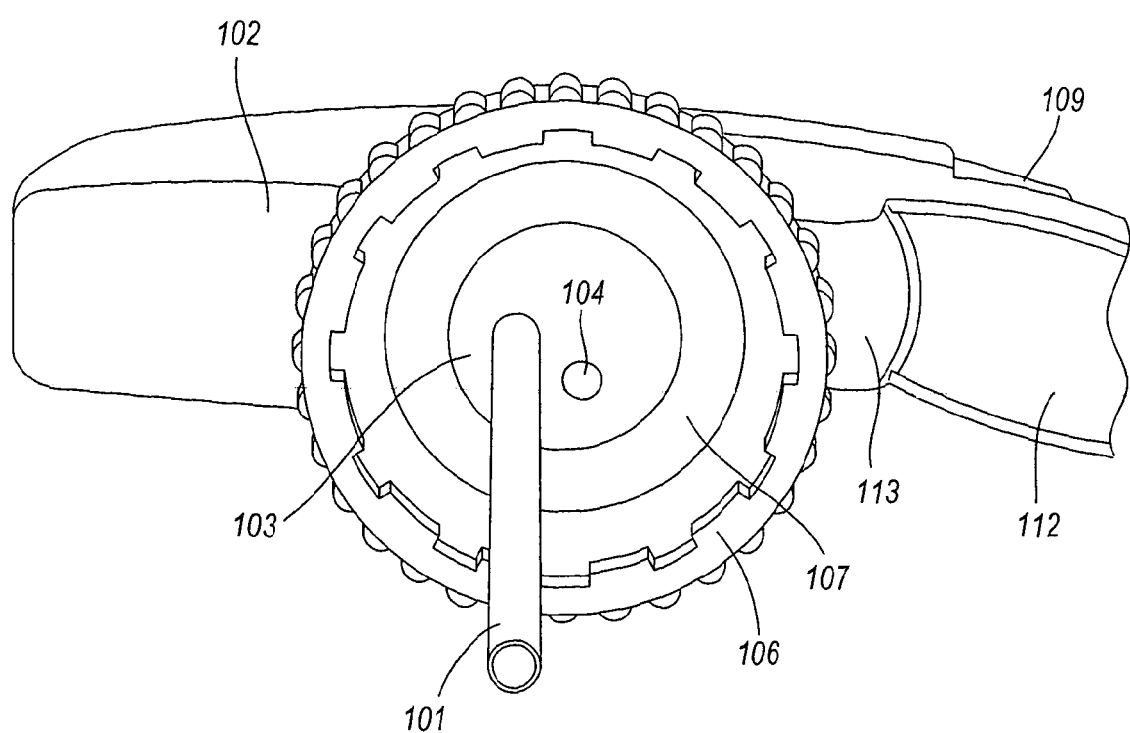
FIG. 4 is a view from below of the part of the dispenser shown in FIGS. 2 and 3.
Figure 5:
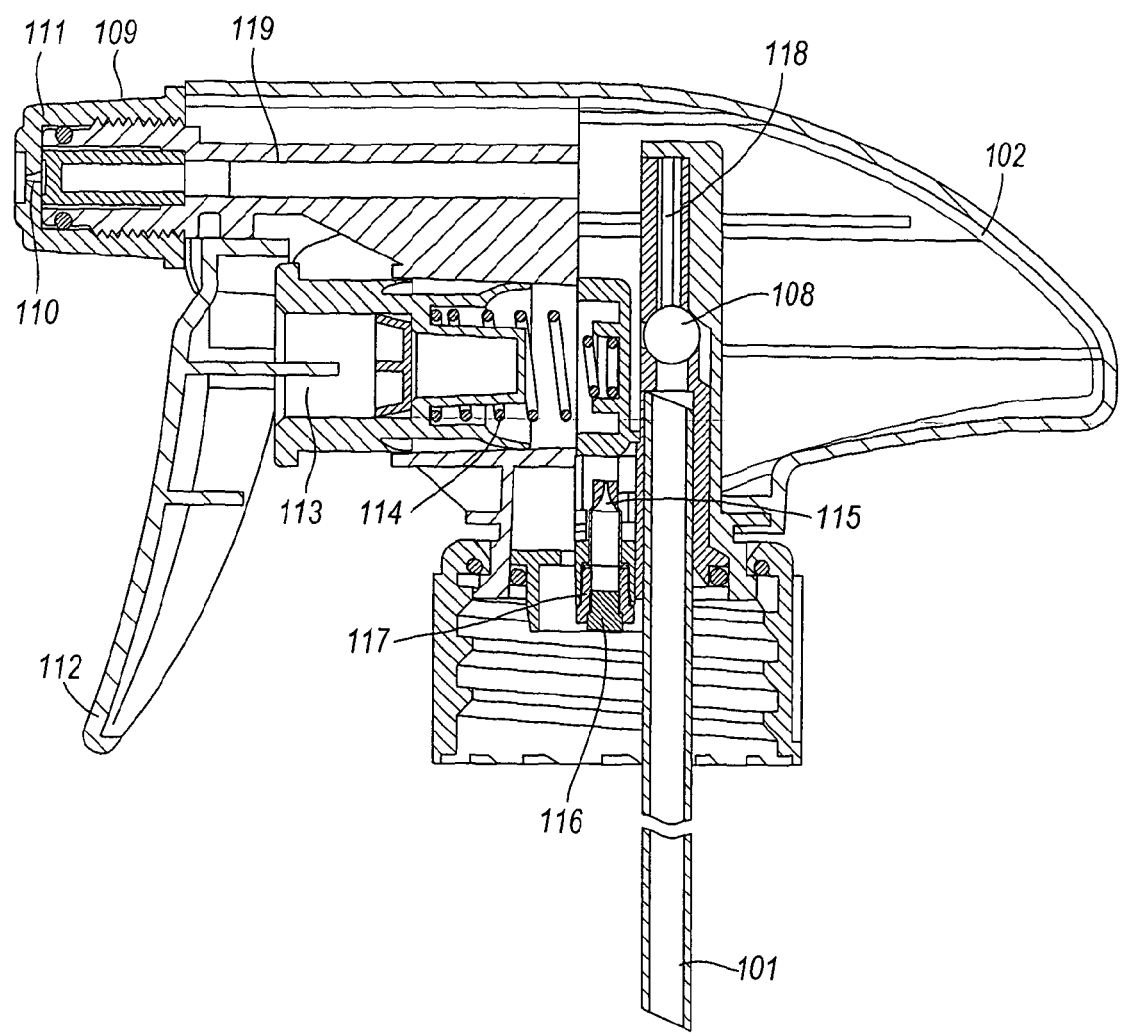
FIG. 5 is a quasi-sectional view of the part of the dispenser of FIGS. 2 to 4.
Figure 6:
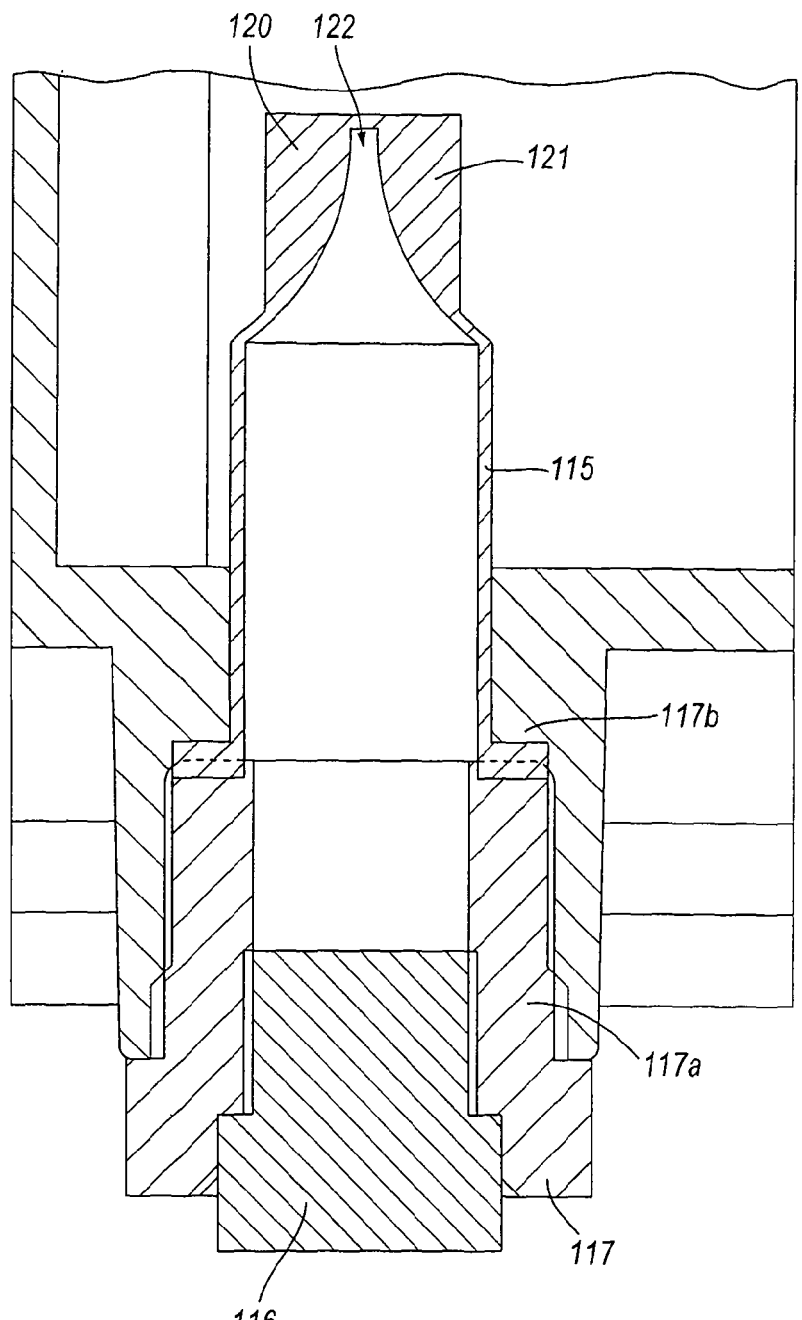
FIG. 6 is a cross-sectional view of a portion of the dispenser of FIGS. 2 to 5 showing the pressure-relief valve and the filter.
Figure 7:
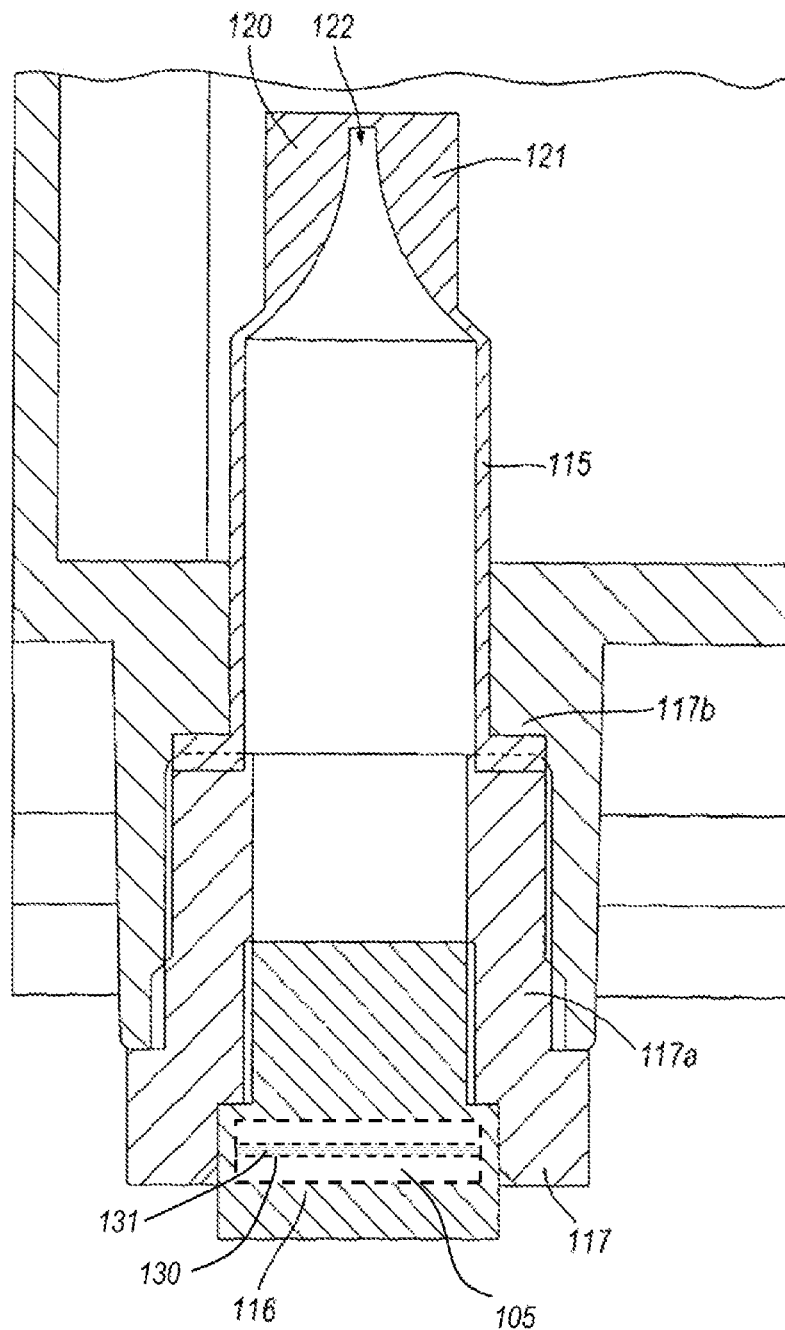
FIG. 7 is a cross-sectional view of a portion of the dispenser of FIGS. 2 to 5 showing the pressure-relief valve and the filter.
Figure 8:
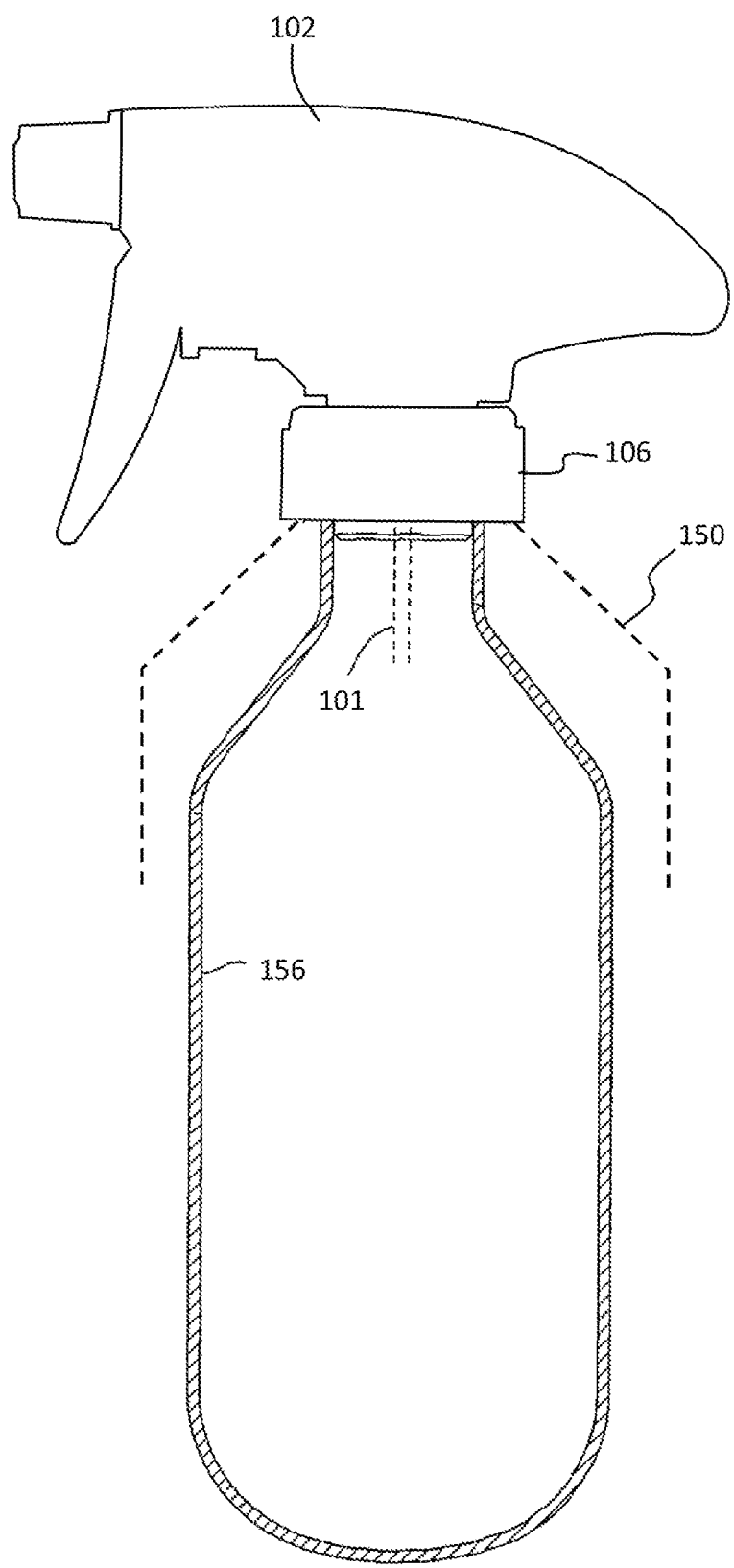
FIG. 8 is a partial schematic side view of the dispenser of FIGS. 2 to 5 connected to a bottle according to an embodiment.

FIG. 1 shows an exploded view of part of a known spray dispenser, as described in GB2391862. For convenience, the operation of the known spray dispenser is now briefly described. The known spray dispenser 1 comprises a flexible, inner vessel 6 in the form of a bag of a plastics material, formed with a convex bottom 7. The inner vessel 6 has a neck region 5 in which the plastics material is welded to a collar 8, thus forming an annular weld 10 around the circumference of the collar 8. A bung 12 is inserted into the collar 8, thus forming a seal between bung and collar. A dip tube (shown as dotted line 9 in FIG. 1) is inserted into the vessel 6 via an aperture in bung 12, there being a seal formed between the dip tube 9 and the bung 12 due to diameter of the dip tube and the resilient nature of the bung. The inner vessel 6 is provided with liquid (not shown) to be dispensed therefrom. The inner vessel 6 is supported by an outer container in the form of a substantially rigid, generally cylindrical plastics bottle 2. The plastics bottle 2 abuts an annular lip 14 provided on collar 8, therefore providing support to the inner vessel 6. The plastics bottle 2 is provided with an aperture 16 which facilitates the passage of air into the plastics bottle and into the space surrounding the inner vessel 6.

The dip tube 9 is associated with a trigger assembly (not shown). The trigger assembly used in the prior art device conforms in general to known trigger-actuated pressure pump arrangements. Actuation of the trigger assembly creates a differential in pressure which draws liquid along the dip tube and dispenses it as a spray. The arrangement of the bung and trigger arrangement ensures that any exhaust air or back pressure does not result in ambient air being drawn into the collapsible container. This inhibits contamination of the contents of the vessel 6 by external contaminants. Because the inner vessel 6 collapses as liquid is dispensed, little or no back pressure exists in the flexible inner vessel. Aperture 16 prevents a partial vacuum being created between the interior wall of plastics bottle 2 and the vessel 6 as the vessel 6 collapses.

An example of a dispenser in accordance with the present invention will now be described with reference to FIGS. 2 to 6. The dispenser comprises a collapsible inner vessel 156 similar to that described above in relation to the prior art and as described in GB2391862. The dispenser also comprises a substantially rigid housing 150 (partially shown in phantom) in the form of a bottle. The bottle is very similar to that described above in relation to the prior art and as described in GB2391862. Whilst the collapsible inner vessel and rigid bottle of GB2391862 were manufactured separately, the collapsible inner vessel and rigid bottle of the example of the spray dispenser of the present invention are made using a single co-extrusion, blow-moulding process. The co-extruded arrangement of the collapsible inner vessel 156 and rigid bottle 150 is commercially available as part of the SteriShield Delivery System (Shield Medicare Limited, Farnham, UK). The inner vessel in the SteriShield system does not have a collar separate from the collar of the rigid bottle.

The dispenser of the present invention comprises a dip tube (101) which extends from the bottom of the collapsible container (not shown) into a dispenser head (102). The dip tube (101) passes through cap (106) via an aperture (not shown) in a plate (103). The dip tube (101) is in sealing engagement with the plate (103) at the aperture (not shown) so as to inhibit passage of air into the container of liquid. The dip tube (101) is in fluid communication with dispenser channel (118). Dispenser channel (118) is provided with a ball valve (108), the operation of which will be described below. Dispenser channel (118) is in fluid communication with dispenser channel (119) which has a nozzle (109) at one end. Nozzle (109) comprises a nozzle aperture (110) for the spray dispensing of fluid and a spray control member (111). The spray control member (111) is mounted relative to the nozzle aperture (110) so that said member is operable to control the spray emitted from the dispenser, as is well-known to those skilled in the art. The spray dispenser further comprises a trigger (112) which is associated with a piston (113). A spring (114) biases the piston and trigger into a forward position.

Liquid is dispensed from the dispenser essentially as described above in relation to the prior art dispenser. Pulling the trigger (112) causes liquid to be pumped from the dispenser as a spray. On releasing the trigger, the spring 114 urges the piston 113 into the forward position. This urges liquid up the dip tube (101) ready to be dispensed on the next spray stroke. The ball valve (108) operates so as to permit fluid flow up through the dip tube (101) into the dispenser head (102) for dispensing, but inhibits ingress of contaminants into the container via the dip tube (101).

The arrangement of the dip tube (101) and sealing member (107) is slightly different from that shown above in FIG. 1 in relation to the prior art. The sealing member (107) comprises an annular washer which, in use, engages with the annular, uppermost surface of the neck of the bottle (not shown) to produce a seal.

The arrangement and operation of the pressure-relief valve and filter are now described. A venting aperture (104) is provided in plate (103). The venting aperture (104) is in gas flow communication with the pressure-relief valve (115) and filter (105), with the filter being in a gas flow path between the venting aperture (104) and the pressure-relief valve (115). The filter (105) is located in a filter housing (116) to facilitate ease of handling. The filter is a membrane (130) of hydrophobic material (Gore® membrane, W. L. Gore and Associates, Newark, USA), with 0.2 micron pores (131) therein. The filter housing (116) is located in a space formed in the valve housing (117). Such an arrangement facilitates ease of placement of the filter relative to the valve. The pressure relief valve 115 is a duck-bill valve which is effectively trapped in place by two parts 117a, 117b of the valve housing 117. The operation of the pressure-relief valve 115 will now be explained briefly. The pressure-relief valve 115 comprises two elastically deformable lips 120, 121 which, in the default state, are urged against one another into a closed state, thus inhibiting ingress of air and contaminants into the container. When there is an over-pressure in a container, the lips 120, 121 are urged apart so that a gas associated with the over-pressure passes out of the vessel through a valve aperture 122, thus relieving the pressure.

The one-way valve 115 therefore permits egress of gas associated with the over-pressure and naturally closes in the absence of over-pressure, therefore inhibiting ingress of air and contaminants into the container. The duckbill valve is made from an elastomer which prevents backflow leakage when minimal backpressure is applied. Furthermore, the elastomer is resilient to gamma radiation which is used to sterilise the container and its contents. The duckbill valve also has the advantage that it can be installed easily into a hole and sealed. Those skilled in the art will realise that the properties of the valve (e.g. the pressure differential at which the valve opens to release pressure and the backpressure at which the valve closes) may be readily optimised by changing the thickness of the elastomer, the shape of the valve and the elastomer from which the valve is made.

The filter 105 provides further protection against ingress of contaminants, and also allows passage therethrough of vapour generated by an overpressure but the filter prevents egress of liquid from the container through the filter. The filter is advantageously sited in a flow path between the valve and the contents of the vessel. Whilst it is possible to site the valve in a flow path between the filter and the contents of the vessel, this is not so desirable because the filter may be prone to clogging, which may inhibit egress of vapour in the event of overpressure.

Those skilled in the art will realise that the present invention is not limited to the type of dispenser mentioned above (i.e. one which comprises a collapsible container sealed to the dispensing mechanism).

Those skilled in the art will also realise that the present invention is not limited to the particular type of valve shown in the example above. For example, a spring-biased pressure relief valve or a reed valve may be used.

It will be apparent to those skilled in the art that an actuator other than a trigger may be used. For example, a button or the like may be used.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

What is claimed is:

1. A dispenser comprising a container for holding a liquid to be dispensed and a dispensing assembly for extracting liquid from said container, the dispensing assembly comprising a pressure-relief valve for release of excessive pressure in the container and a filter arranged to permit egress of gas from the container through the filter and through the pressure-relief valve, the filter inhibiting egress of liquid from the container through the filter, the pressure-relief valve being closed in the absence of excessive pressure to inhibit ingress of air and contaminants into the container wherein: the filter is in a gas flow path between the interior of the container and the pressure-relief valve, or the pressure-relief valve is in a gas flow path between the interior of the container and the filter.

2. A dispenser according to claim 1, wherein the filter inhibits ingress of particulate into the container.

3. A dispenser according to claim 2, wherein the filter comprises pores which permit passage therethrough of gas, but inhibit passage therethrough of particulate.

4. A dispenser according to claim 3, wherein the pore size is less than 10 microns at its mean greatest dimension.

5. A dispenser according to claim 3, wherein the pore size is less than 1 micron at its mean greatest dimension.

6. A dispenser according to claim 1, wherein the filter is located within a filter housing.

7. A dispenser according to claim 1, wherein the container comprises a fluid containment portion which is collapsible.

8. A dispenser according to claim 7, wherein the container comprises a collar.

9. A dispenser according to claim 1, wherein the container comprises a container seal-forming surface and the spray dispenser comprises a sealing member for forming a seal against the container seal-forming surface to inhibit ingress of air into the container.

10. A dispenser according to claim 9, wherein the dispenser assembly comprises the sealing member.

11. A dispenser according to claim 1, wherein the pressure-relief valve comprises a diaphragm valve, a spring valve, a butterfly valve, a swing valve, a ball check valve or a duckbill valve.

12. A dispenser according to claim 1, wherein the dispenser is provided with a closure for inhibiting access to the container.

13. A dispenser according to claim 12, wherein the dispensing assembly comprises the closure.

14. A dispenser according to claim 12, wherein the closure is provided with both the pressure-relief valve and the filter.

15. A dispenser according to claim 1 comprising a housing for enclosing the container.

16. A dispenser according to claim 15, wherein the housing supports the container.

17. A dispenser according to claim 15, comprising a closure being removably attachable to the housing.

18. A dispenser according to claim 1, the dispensing assembly comprising a dispensing line, wherein the dispensing line is in a gas-tight sealing engagement with a dispensing line seal provider.

19. A dispenser according to claim 18, wherein the dispensing line seal provider is in the form of an apertured plate, the plate being provided with an aperture which receives the dispensing line in sealing engagement.

20. A dispenser according to claim 1, wherein the dispensing assembly is mountable onto, and dismountable from, the container.

21. A dispenser according to claim 1, the filter comprising a hydrophobic membrane.

22. A dispenser according to claim 1, wherein the container is rigid.

23. A dispenser according to claim 1, the filter comprising an oleophilic membrane.

24. A dispenser according to claim 1, wherein the container is plastic.

25. A dispenser according to claim 1, wherein the dispensing assembly is mountable onto the container.

26. A dispensing assembly for use in a dispenser to dispense liquid from a container, the dispensing assembly comprising a pressure-relief valve for release of excessive pressure in a container to which the dispensing assembly is fitted and a filter arranged to permit egress of gas from the container through the filter and through the pressure-relief valve, the filter inhibiting egress of liquid from a container to which the dispensing assembly is fitted, the pressure-relief valve being closed in the absence of excessive pressure in a container to which the dispensing assembly is fitted so as to inhibit ingress and air and contaminants into a container to which the dispensing assembly is fitted, wherein the filter is in a gas flow path between the interior of the container to which the dispensing assembly is fitted and the pressure-relief valve, or the pressure-relief valve is in a gas flow path between the interior of the container to which the dispensing assembly is fitted and the filter.

27. A dispensing assembly according to claim 26, wherein the filter is located within a filter housing.

28. The dispensing assembly according to claim 26, further comprising a sealing member.

29. The dispensing assembly according to claim 26, wherein the pressure-relief valve is selected from the group consisting of a diaphragm valve, a spring valve, a butterfly valve, a swing valve, a ball check valve, and a duckbill valve.

30. The dispensing assembly according to claim 26, further comprising a closure for inhibiting access to the container.

31. The dispensing assembly according to claim 30, wherein the closure is provided with both the pressure-relief valve and the filter.

32. The dispensing assembly according to claim 26, further comprising a dispensing line in a gas-tight sealing engagement with a dispensing line seal provider.

33. The dispensing assembly of claim 32, wherein the dispensing line seal provider is in the form of an apertured plate, the plate being provided with an aperture which receives the dispensing line in sealing engagement.

34. The dispensing assembly of claim 26, wherein the filter comprises a hydrophobic membrane.

35. The dispensing assembly of claim 26, wherein the filter comprises an oleophilic membrane.

36. The dispensing assembly of claim 26, the filter further comprising pores.

37. The dispensing assembly of claim 36, wherein the pore size is less than 10 microns at its mean greatest dimension.

38. The dispensing assembly of claim 36, wherein the pore size is less than 1 micron at its mean greatest dimension.

* * * * *

UNITED STATES PATENT AND TRADEMARK OFFICE
CERTIFICATE OF CORRECTION

PATENT NO. : 10,556,247 B2  
APPLICATION NO. : 15/477875  
DATED : February 2, 2021  
INVENTOR(S) : Syson et al.

Page 1 of 1

It is certified that error appears in the above-identified patent and that said Letters Patent is hereby corrected as shown below:

In the Specification

Column 1, Line 5 Please correct the priority information as noted below:
This application is a continuation of U.S. Application No. 14/939,810, filed 12 November 2015, now U.S. Patent No. 9,649,648, issued May 16, 2017, which is a continuation of U.S. Application No. 13/502,954, filed 26 September 2012, now U.S. Patent No. 9,211,557, which is a National Stage Application of PCT/GB2010/051761, filed 19 October 2010, which claims benefit of Serial No. 0918296.5, filed 19 October 2009 in the United Kingdom and which applications are incorporated herein by reference. To the extent appropriate, a claim of priority is made to each of the above disclosed applications.

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*